US008600504B2

United States Patent
Hopper et al.

(10) Patent No.: US 8,600,504 B2
(45) Date of Patent: Dec. 3, 2013

(54) PHYSIOLOGIC DEMAND DRIVEN PACING

(75) Inventors: Donald L. Hopper, Maple Grove, MN (US); Yinghong Yu, Shoreview, MN (US); David J. Ternes, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 122 days.

(21) Appl. No.: 13/161,851

(22) Filed: Jun. 16, 2011

(65) Prior Publication Data

US 2012/0004698 A1 Jan. 5, 2012

Related U.S. Application Data

(60) Provisional application No. 61/361,015, filed on Jul. 2, 2010.

(51) Int. Cl.
*A61N 1/365* (2006.01)

(52) U.S. Cl.
USPC ...... 607/25; 607/9; 607/11; 607/17; 607/115; 607/119; 607/123; 600/508; 600/509; 600/510; 600/515; 600/516; 600/517

(58) Field of Classification Search
USPC ........... 607/1–2, 9, 11, 17, 25, 115, 119, 123; 600/508–510, 515–517
See application file for complete search history.

(56) References Cited

U.S. PATENT DOCUMENTS

| | | | |
|---|---|---|---|
| 4,712,179 A | 12/1987 | Heimer | |
| 4,809,697 A | 3/1989 | Causey, III et al. | |
| 4,825,869 A | 5/1989 | Sasmor et al. | |
| 4,928,688 A | 5/1990 | Mower | |
| 5,097,831 A | 3/1992 | Lekholm | |
| 5,174,289 A | 12/1992 | Cohen | |
| 5,226,413 A | 7/1993 | Bennett et al. | |
| 5,251,626 A | 10/1993 | Nickolls et al. | |
| 5,267,560 A | 12/1993 | Cohen | |
| 5,282,838 A | 2/1994 | Hauser et al. | |
| 5,292,341 A | 3/1994 | Snell | |
| 5,321,618 A | 6/1994 | Gessman | |
| 5,372,607 A | 12/1994 | Stone et al. | |
| 5,421,830 A | 6/1995 | Epstein et al. | |
| 5,431,691 A | 7/1995 | Snell et al. | |
| 5,456,952 A | 10/1995 | Garza et al. | |
| 5,487,752 A | 1/1996 | Salo et al. | |
| 5,507,782 A | 4/1996 | Kieval et al. | |
| 5,540,727 A | 7/1996 | Tockman et al. | |
| 5,549,654 A | 8/1996 | Powell | |

(Continued)

FOREIGN PATENT DOCUMENTS

| | | |
|---|---|---|
| WO | WO-0041765 | 7/2000 |
| WO | WO-0041766 | 7/2000 |

OTHER PUBLICATIONS

"U.S. Appl. No. 09/748,791, Advisory Action mailed Aug. 4, 2004", 3 pgs.

(Continued)

*Primary Examiner* — Deborah Malamud

(74) *Attorney, Agent, or Firm* — Schwegman Lundberg & Woessner, P.A.

(57) ABSTRACT

Physiologic demand driven pacing can be used to maintain cardiac synchrony and improve hemodynamic function in patients with heart failure.

20 Claims, 5 Drawing Sheets

(56) References Cited

U.S. PATENT DOCUMENTS

| | | | |
|---|---|---|---|
| 5,594,638 A | 1/1997 | Iliff | |
| 5,607,460 A | 3/1997 | Kroll et al. | |
| 5,630,835 A | 5/1997 | Brownlee | |
| 5,690,690 A | 11/1997 | Nappholz et al. | |
| 5,693,076 A | 12/1997 | Kaemmerer | |
| 5,697,959 A | 12/1997 | Poore | |
| 5,713,937 A | 2/1998 | Nappholz et al. | |
| 5,716,382 A | 2/1998 | Snell | |
| 5,792,203 A | 8/1998 | Schroeppel | |
| 5,800,473 A | 9/1998 | Faisandier | |
| 5,817,137 A | 10/1998 | Kaemmerer | |
| 5,833,623 A | 11/1998 | Mann et al. | |
| 5,891,178 A | 4/1999 | Mann et al. | |
| 5,911,132 A | 6/1999 | Sloane et al. | |
| 6,016,442 A | 1/2000 | Hsu et al. | |
| 6,070,101 A | 5/2000 | Struble et al. | |
| 6,091,990 A | 7/2000 | Hsu et al. | |
| 6,129,744 A | 10/2000 | Boute | |
| 6,141,586 A | 10/2000 | Mower | |
| 6,144,880 A | 11/2000 | Ding et al. | |
| 6,148,234 A | 11/2000 | Struble | |
| 6,168,563 B1 | 1/2001 | Brown | |
| 6,249,705 B1 | 6/2001 | Snell | |
| 6,272,377 B1 | 8/2001 | Sweeney et al. | |
| 6,280,389 B1 | 8/2001 | Ding et al. | |
| 6,285,907 B1 | 9/2001 | Kramer et al. | |
| 6,304,773 B1 | 10/2001 | Taylor et al. | |
| 6,351,673 B1 | 2/2002 | Ding et al. | |
| 6,351,675 B1 | 2/2002 | Tholen et al. | |
| 6,360,127 B1 | 3/2002 | Ding et al. | |
| 6,370,427 B1 | 4/2002 | Alt et al. | |
| 6,400,982 B2 | 6/2002 | Sweeney et al. | |
| 6,411,847 B1 | 6/2002 | Mower | |
| 6,442,432 B2 | 8/2002 | Lee | |
| 6,442,433 B1 | 8/2002 | Linberg | |
| 6,497,655 B1 | 12/2002 | Linberg et al. | |
| 6,526,313 B2 | 2/2003 | Sweeney et al. | |
| 6,542,775 B2 | 4/2003 | Ding et al. | |
| RE38,119 E | 5/2003 | Mower | |
| 6,564,104 B2 | 5/2003 | Nelson et al. | |
| 6,597,951 B2 | 7/2003 | Kramer et al. | |
| 6,622,040 B2 | 9/2003 | Ding et al. | |
| 6,625,494 B2 | 9/2003 | Fang et al. | |
| 6,668,194 B2 | 12/2003 | VanHout | |
| 6,669,631 B2 | 12/2003 | Norris et al. | |
| 6,684,103 B2 | 1/2004 | Ding et al. | |
| 6,708,058 B2 | 3/2004 | Kim et al. | |
| 6,804,555 B2 | 10/2004 | Warkentin | |
| 6,856,836 B2 | 2/2005 | Ding et al. | |
| 6,859,665 B2 | 2/2005 | Ding et al. | |
| 6,915,160 B2 | 7/2005 | Auricchio et al. | |
| 6,961,616 B2 | 11/2005 | Kramer et al. | |
| 6,999,815 B2 | 2/2006 | Ding et al. | |
| 7,003,349 B1 | 2/2006 | Andersson et al. | |
| 7,013,176 B2 | 3/2006 | Ding et al. | |
| 7,070,562 B2 | 7/2006 | Bardy | |
| 7,110,817 B2 | 9/2006 | Yu et al. | |
| 7,123,960 B2 | 10/2006 | Ding et al. | |
| 7,136,707 B2 | 11/2006 | Hall et al. | |
| 7,158,830 B2 | 1/2007 | Yu et al. | |
| 7,181,285 B2 | 2/2007 | Lindh et al. | |
| 7,184,835 B2 | 2/2007 | Kramer et al. | |
| 7,203,540 B2 | 4/2007 | Ding et al. | |
| 7,231,248 B2 | 6/2007 | Kramer et al. | |
| 7,310,554 B2 | 12/2007 | Kramer et al. | |
| 7,383,088 B2 | 6/2008 | Spinelli et al. | |
| 7,532,924 B2 | 5/2009 | Ternes | |
| 7,546,162 B2 | 6/2009 | Ding et al. | |
| 7,630,764 B2 | 12/2009 | Ding et al. | |
| 7,672,721 B2 | 3/2010 | Chirife et al. | |
| 7,720,537 B2 | 5/2010 | Sheldon et al. | |
| 7,769,449 B2 | 8/2010 | Chirife et al. | |
| 7,899,533 B2 | 3/2011 | Chirife et al. | |
| 7,899,534 B2 | 3/2011 | Lindh et al. | |
| 8,099,165 B2 | 1/2012 | Lindh et al. | |
| 8,386,036 B2 | 2/2013 | Lindh et al. | |
| 2001/0031997 A1 | 10/2001 | Lee | |
| 2001/0039375 A1 | 11/2001 | Lee et al. | |
| 2001/0039503 A1 | 11/2001 | Chan et al. | |
| 2002/0016550 A1 | 2/2002 | Sweeney et al. | |
| 2002/0120311 A1 | 8/2002 | Lindh et al. | |
| 2002/0123672 A1 | 9/2002 | Christophersom et al. | |
| 2003/0050803 A1 | 3/2003 | Marchosky | |
| 2003/0088290 A1 | 5/2003 | Spinelli et al. | |
| 2004/0122487 A1 | 6/2004 | Hatlestad et al. | |
| 2004/0133080 A1 | 7/2004 | Mazar | |
| 2004/0133246 A1 | 7/2004 | Ding et al. | |
| 2004/0143304 A1 | 7/2004 | Hall et al. | |
| 2007/0250125 A1 | 10/2007 | Lindh et al. | |
| 2008/0027489 A1 | 1/2008 | Sheldon et al. | |
| 2008/0077031 A1 | 3/2008 | Spinelli et al. | |
| 2009/0005828 A1 | 1/2009 | Levine | |
| 2009/0048637 A1* | 2/2009 | Ni et al. | 607/9 |
| 2009/0248104 A1 | 10/2009 | Ding et al. | |
| 2010/0222840 A1 | 9/2010 | Chirife et al. | |
| 2011/0022108 A1 | 1/2011 | Chirife et al. | |
| 2011/0137368 A1 | 6/2011 | Lindh et al. | |
| 2012/0083854 A1 | 4/2012 | Lindh et al. | |

OTHER PUBLICATIONS

"U.S. Appl. No. 09/748,791, Final Office Action mailed Mar. 9, 2004", 6 pgs.

"U.S. Appl. No. 09/748,791, Final Office Action mailed Aug. 23, 2005", 6 pgs.

"U.S. Appl. No. 09/748,791, Non-Final Office Action mailed Feb. 3, 2005", 6 pgs.

"U.S. Appl. No. 09/748,791, Non-Final Office Action mailed Feb. 10, 2006", 9 pgs.

"U.S. Appl. No. 09/748,791, Non-Final Office Action mailed Feb. 21, 2003", 9 pgs.

"U.S. Appl. No. 09/748,791, Non-Final Office Action mailed Aug. 28, 2002", 7 pgs.

"U.S. Appl. No. 09/748,791, Non-Final Office Action mailed Sep. 17, 2003", 8 pgs.

"U.S. Appl. No. 09/748,791, Notice of Allowance mailed Sep. 3, 2004", 7 pgs.

"U.S. Appl. No. 09/748,791, Notice of Allowance mailed Sep. 20, 2006", 5 pgs.

"U.S. Appl. No. 09/748,791, Preliminary Amendment filed Feb. 21, 2001", 2 pgs.

"U.S. Appl. No. 09/748,791, Response filed May 10, 2006 to Non-Final Office Action mailed Feb. 10, 2006", 8 pgs.

"U.S. Appl. No. 09/748,791, Response filed Jul. 5, 2005 to Non-Final Office Action mailed Feb. 3, 2005", 7 pgs.

"U.S. Appl. No. 09/748,791, Response filed Jul. 9, 2004 to Final Office Action mailed Mar. 9, 2004", 11 pgs.

"U.S. Appl. No. 09/748,791, Response filed Jul. 21, 2003 to Non-Final Office Action mailed Feb. 21, 2003", 15 pgs.

"U.S. Appl. No. 09/748,791, Response filed Nov. 23, 2005 to Final Office Action mailed Aug. 23, 2005", 7 pgs.

"U.S. Appl. No. 09/748,791, Response filed Nov. 25, 2002 to Non-Final Office Action mailed Aug. 28, 2002", 7 pgs.

"U.S. Appl. No. 09/748,791, Response filed Dec. 17, 2003 to Non-Final Office Action mailed Sep. 17, 2003", 10 pgs.

"U.S. Appl. No. 11/624,035, Notice of Allowance mailed Oct. 25, 2010", 9 pgs.

"Landmark study finds high resting heart associated with shorter life expectancy", Medicine & Health/Diseases http://www.physorg.com/news/2010-10-landmark-high-resting-heart-shorter.html, (Oct. 26, 2010), 2 pgs.

Abraham, W T, "Cardiac Resynchronization in Chronic Heart Failure", New England Journal of Medicine, 346(24), (Jul. 13, 2002), 1845-1853.

Auricchio, A., "Effect of Pacing Chamber and Atrioventricular Delay on Acute Systolic Function of Paced Patients With Congestive Heart Failure", Circulation, 99(23), (Jun. 15, 1999), 2993-3001.

Auricchio, A., et al., "Long-term clinical effect of hemodynamically optimized cardiac resynchronization therapy in patients with heart failure and ventricular conduction delay", J Am Coll Cardiol., 39, (Jun. 19, 2002), 2026-33.

(56) References Cited

OTHER PUBLICATIONS

Boriani, G., et al., "Randomized comparison of simultaneous biventricular stimulation versus optimized interventricular delay in cardiac resynchronization therapy", Am Heart J., 151(5), (May 2006), 1050-8.

Bristow, M. R, et al., "Cardiac-resynchronization therapy with or without an implantable defibrillator in advanced chronic heart failure", N Engl J Med., 350, (May 20, 2004), 2140-50.

De Lurgio, D. B., et al., "A comparison of cardiac resynchronization by sequential biventricular pacing and left ventricular pacing to simultaneous biventricular pacing: rationale and design of the DECREASE-HF clinical trial", J Card Fail., 11, (Apr. 2005), 233-9.

Gold, M. R, et al., "A prospective comparison of AV delay programming methods for hemodynamic optimization during cardiac resynchronization therapy", J Cardiovasc Electrophysiol., 18(5), (May 2007), 490-6.

Hall, Jeffrey A., et al., "Recordable Macros for Pacemaker Follow-Up", U.S. Appl. No. 10/348,191, filed Jan. 21, 2003, 17 pgs.

Hunt, S. A, "ACC/AHA 2005 guideline update for the diagnosis and management of chronic heart failure in the adult", J Am Coll Cardiol., 46(6), (Sep. 20, 2005), e1-82.

Kass, D. A, "Cardiac resynchronization therapy", J Cardiovasc Electrophysiol., 16(Suppl 1), (Sep. 2005), S35-41.

Kass, D. A., "Improved Left Ventricular Mechanics From Acute VDD Pacing in Patients With Dilated Cardiomyopathy and Ventricular Conduction Delay", Circulation, 99(12), (Mar. 30, 1999), 1567-1573.

Linde, C., et al., "Long-term benefits of biventricular pacing in congestive heart failure: results from the MUltisite STimulation in cardiomyopathy (MUSTIC) study", J Am Coll Cardiol., 40, (Jul. 3, 2002), 111-8.

Mower, Morton, , U.S. Patent Office Patent Application Information Retrieval search results for U.S. Appl. No. 10/214,474, filed Aug. 8, 2002, entitled "Method and Apparatus for Treating Hemodynamic Disfunction", 3.

Perego, G. B, et al., "Simultaneous vs. sequential biventricular pacing in dilated cardiomyopathy: an acute hemodynamic study", Eur J Heart Fail., 5(3), (Jun. 2003), 305-13.

Rao, R. K, et al., "Reduced ventricular volumes and improved systolic function with cardiac resynchronization therapy: a randomized trial comparing simultaneous biventricular pacing, sequential biventricular pacing, and left ventricular pacing", Circulation, 115(16), (Apr. 24, 2007), 2136-2144.

Saxon, L. A, et al., "Effects of long-term biventricular stimulation for resynchronization on echocardiographic measures of remodeling", Circulation, 105(11), (Mar. 19, 2002), 1304-10.

Sharma, A. D, et al., "Percent Right Ventricular Pacing Predicts Outcomes in the DAVID Trial", Heart Rhythm, 2(8), (2005), 830-834.

Sogaard, P., et al., "Sequential versus simultaneous biventricular resynchronization for severe heart failure: evaluation by tissue Doppler imaging", Circulation, 106(16), (Oct. 15, 2002), 2078-84.

Stellbrink, Christoph, "Impact of Cardiac Resynchronization Therapy Using Hemodynamically Optimized Pacing on Left Ventricular Remodeling in Patients With Congestive Heart Failure and Ventricular Conduction Disturbances", Journal of the American College of Cardiology, vol. 38, No. 7, (Dec. 2001), 1957-1965.

Van Gelder, B. M., et al., "Effect of optimizing the VV interval on left ventricular contractility in cardiac resynchronization therapy", Am J Cardiol., 93(12), (Jun. 15, 2004), 1500-3.

Vanderheyden, M., et al., "Tailored echocardiographic interventricular delay programming further optimizes left ventricular performance after cardiac resynchronization therapy", Heart Rhythm, 2(10), (Oct. 2005), 1066-72.

Whinnett, Z. I, et al., "Haemodynamic effects of changes in atrioventricular and interventricular delay in cardiac resynchronisation therapy show a consistent pattern: analysis of shape, magnitude and relative importance of atrioventricular and interventricular delay", Heart, 92(11), (Nov. 2006), 1628-34.

Yu, C. M, et al., "Tissue Doppler Echocardiographic Evidence of Reverse Remodeling and Improved Synchronicity by Simultaneously Delaying Regional Contraction After Biventricular Pacing Therapy in Heart Failure", Circulation, 105(4), (Jan. 29, 2002), 438-445.

Yu, Yinghong, et al., "Biventricular mechanical asynchrony predicts hemodynamic effects of uni- and biventricular pacing", Am J Physiol Heart Circ Physiol, vol. 285, (2003), H2788-H2796.

"U.S. Appl. No. 13/027,681, Notice of Allowance mailed Sep. 22, 2011", 6 pgs.

"U.S. Appl. No. 13/027,68, Response filed Aug. 26, 2011 to Non-Final Office Action mailed May 26, 2011", 13 pgs.

"U.S. Appl. No. 13/326,681, Non Final Office Action mailed Jul. 11, 2012", 10 pgs.

"U.S. Appl. No. 13/326,681, Notice of Allowance mailed Oct. 29, 2012", 6 pgs.

"U.S. Appl. No. 13/326,681, Response filed Oct. 5, 2012 to Non Final Office Action mailed Jul. 11, 2012", 13 pgs.

US 6,527,714, 03/2003, Bardy (withdrawn)

\* cited by examiner

PHYSIOLOGIC DEMAND DRIVEN PACING

CROSS-REFERENCE TO RELATED APPLICATIONS

This application claims the benefit of U.S. Provisional Application No. 61/361,015, filed on Jul. 2, 2010, under 35 U.S.C. §119(e), which is incorporated herein by reference in its entirety.

BACKGROUND

Cardiac rhythm management (CRM) devices include implantable or ambulatory devices such as pacemakers, cardioverter defibrillators, and devices that provide a combination of pacing and defibrillation, including cardiac resynchronization therapy (CRT). These devices can be used to detect and treat heart failure. Lindh et al. U.S. Pat. No. 7,181,285, entitled EXPERT SYSTEM AND METHOD, mentions a medical device programmer and a method of operation in which a QRS complex duration interval can be used to suggest one or more ventricular chambers in which to provide pacing pulses. (See Lindh et al. U.S. Pat. No. 7,181,285 at Abstract.) Lindh et al. U.S. Pat. No. 7,181,285 also mentions that pacing intervals for an AV delay are suggested based on measured P-R intervals. (See id.)

OVERVIEW

This document describes, among other things, an apparatus and method in which physiologic demand driven pacing can be used to maintain cardiac synchrony and improve hemodynamic function in patients with heart failure.

Example 1 can include subject matter that can include an apparatus comprising: a data input configured to receive a duration of a QRS complex; ventricular pacing circuitry configured to provide ventricular pacing pulses in response to expiration of a specified atrioventricular (AV) delay; and control circuitry configured to use information about the duration of the QRS complex to: intermittently extend the specified AV delay to promote intrinsic ventricular contractions; and shorten the specified AV delay to provide a shortened AV delay, wherein the shortened AV delay is less than the specified AV delay.

In Example 2, the subject matter of Example 1 can optionally include the control circuitry configured to intermittently extend the specified AV delay when the duration of the QRS complex is less than a specified threshold value.

In Example 3, the subject matter of any one of Examples 1-2 can optionally include the control circuitry configured to shorten the specified AV delay when the duration of the QRS complex is greater than a specified threshold value.

In Example 4, the subject matter of any one of Examples 1-3 can optionally include the control circuitry configured to use the duration of the QRS complex to automatically adjust at least one of extending or shortening the specified AV delay.

In Example 5, the subject matter of any one of Examples 1-4 can optionally include a data input configured to receive a heart rate; wherein the control circuitry is configured to: compare the duration of the QRS complex to a first specified threshold value; determine a heart rate associated with the first specified threshold value; use the heart rate associated with the first specified threshold value to determine a second specified threshold value; compare a subject's heart rate to the second specified threshold value; when the subject's heart rate is less than the second specified threshold value, intermittently extend the specified AV delay to promote intrinsic ventricular contractions; and when the subject's heart rate is greater than or equal to the second specified threshold value, provide ventricular pacing pulses in response to expiration of the shortened AV delay, wherein the shortened AV delay is less than the specified AV delay.

In Example 6, the subject matter of any one of Examples 1-5 can optionally include the control circuitry configured to determine a heart rate associated with the first specified threshold value by determining a heart rate measured concurrently with the duration of the QRS complex when the duration of the QRS complex is equal to the first specified threshold value.

In Example 7, the subject matter of any one of Examples 1-6 can optionally include a data input configured to receive an intrinsic PR interval duration; wherein the control circuitry is configured to: compare the intrinsic PR interval duration to a first specified threshold; compare the duration of the QRS complex to a second specified threshold; when the PR interval duration is less than the first specified threshold and the duration of the QRS complex is less than the second specified threshold, withhold ventricular pacing pulses; when the PR interval duration is greater than the first specified threshold and the duration of the QRS complex is less than the second specified threshold, intermittently extend the specified AV delay to promote intrinsic ventricular contractions; and, when the duration of the QRS complex is greater than the second specified threshold, provide ventricular pacing pulses in response to expiration of the shortened AV delay, wherein the shortened AV delay is less than the specified AV delay.

In Example 8, the subject matter of any one of Examples 1-7 can optionally include the control circuitry configured to use the PR interval duration and the duration of the QRS complex to automatically adjust at least one of extending or shortening the specified AV delay.

In Example 9, the subject matter of any one of Examples 1-8 can optionally include ventricular pacing pulses provided to at least one of a left ventricle or a right ventricle.

In Example 10, the subject matter of any one of Examples 1-9 can optionally include a user interface, coupled to the control circuitry to receive information about at least one of the QRS complex, the specified AV delay, or ventricular pacing pulses, and to provide the information to a user or automated process.

Example 11 can include, or can optionally be combined with any one of Examples 1-10 to include, subject matter (e.g., a method, a device-readable medium, or a means for performing one or more functions) that can include measuring a duration of a QRS complex; providing ventricular pacing pulses in response to expiration of a specified atrioventricular (AV) delay; and using information about the duration of the QRS complex to: intermittently extend the specified AV delay to promote intrinsic ventricular contractions; and shorten the specified AV delay to provide a shortened AV delay, wherein the shortened AV delay is less than the specified AV delay.

In Example 12, the subject matter of any one of Examples 1-11 can optionally include intermittently extending the specified AV delay when the duration of the QRS complex is less than a specified threshold value.

In Example 13, the subject matter of any one of Examples 1-12 can optionally include shortening the specified AV delay when the duration of the QRS complex is greater than a specified threshold value.

In Example 14, the subject matter of any one of Examples 1-13 can optionally include using the duration of the QRS complex to automatically adjust at least one of extending or shortening the specified AV delay.

In Example 15, the subject matter of any one of Examples 1-14 can optionally include measuring a heart rate; comparing the duration of the QRS complex to a first specified threshold value; determining a heart rate associated with the first specified threshold value; using the heart rate associated with the first specified threshold value to determine a second specified threshold value; comparing a subject's heart rate to the second specified threshold value; when the subject's heart rate is less than the second specified threshold value, intermittently extending the specified AV delay to promote intrinsic ventricular contractions; and when the subject's heart rate is greater than or equal to the second specified threshold value, providing ventricular pacing pulses in response to expiration of the shortened AV delay, wherein the shortened AV delay is less than the specified AV delay.

In Example 16, the subject matter of any one of Examples 1-15 can optionally include determining a heart rate associated with the first specified threshold value by determining a heart rate measured concurrently with the duration of the QRS complex when the duration of the QRS complex is equal to the first specified threshold value.

In Example 17, the subject matter of any one of Examples 1-16 can optionally include measuring an intrinsic PR interval duration; comparing the intrinsic PR interval duration to a first specified threshold; comparing the duration of the QRS complex to a second specified threshold; when the PR interval duration is less than the first specified threshold and the duration of the QRS complex is less than the second specified threshold, withholding ventricular pacing pulses; when the PR interval duration is greater than the first specified threshold and the duration of the QRS complex is less than the second specified threshold, intermittently extending the specified AV delay to promote intrinsic ventricular contractions; and, when the duration of the QRS complex is greater than the second specified threshold, providing ventricular pacing pulses in response to expiration of the shortened AV delay, wherein the shortened AV delay is less than the specified AV delay.

In Example 18, the subject matter of any one of Examples 1-17 can optionally include using the PR interval duration and the duration of the QRS complex to automatically adjust at least one of extending or shortening the specified AV delay.

In Example 19, the subject matter of any one of Examples 1-18 can optionally include providing ventricular pacing pulses to at least one of a left ventricle or a right ventricle.

In Example 20, the subject matter of any one of Examples 1-19 can optionally include providing information about at least one of the QRS complex, the specified AV delay, or ventricular pacing pulses to a user or automated process.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present inventors have recognized, among other things, that an apparatus and method for providing physiologic demand driven pacing can be used to maintain cardiac synchrony and improve hemodynamic function in patients with heart failure. In heart failure patients for whom CRT has been indicated, 100% biventricular pacing can be desirable. However, changes over time in the cardiac conduction system caused by remodeling or changes in medication, diet, or activity, for example, can change patients' need for biventricular pacing. Thus, patients may not need biventricular pacing if they can maintain a reasonable intrinsic PR interval and reasonable ventricular synchrony, such as can be indicated by QRS width.

Figure 1:
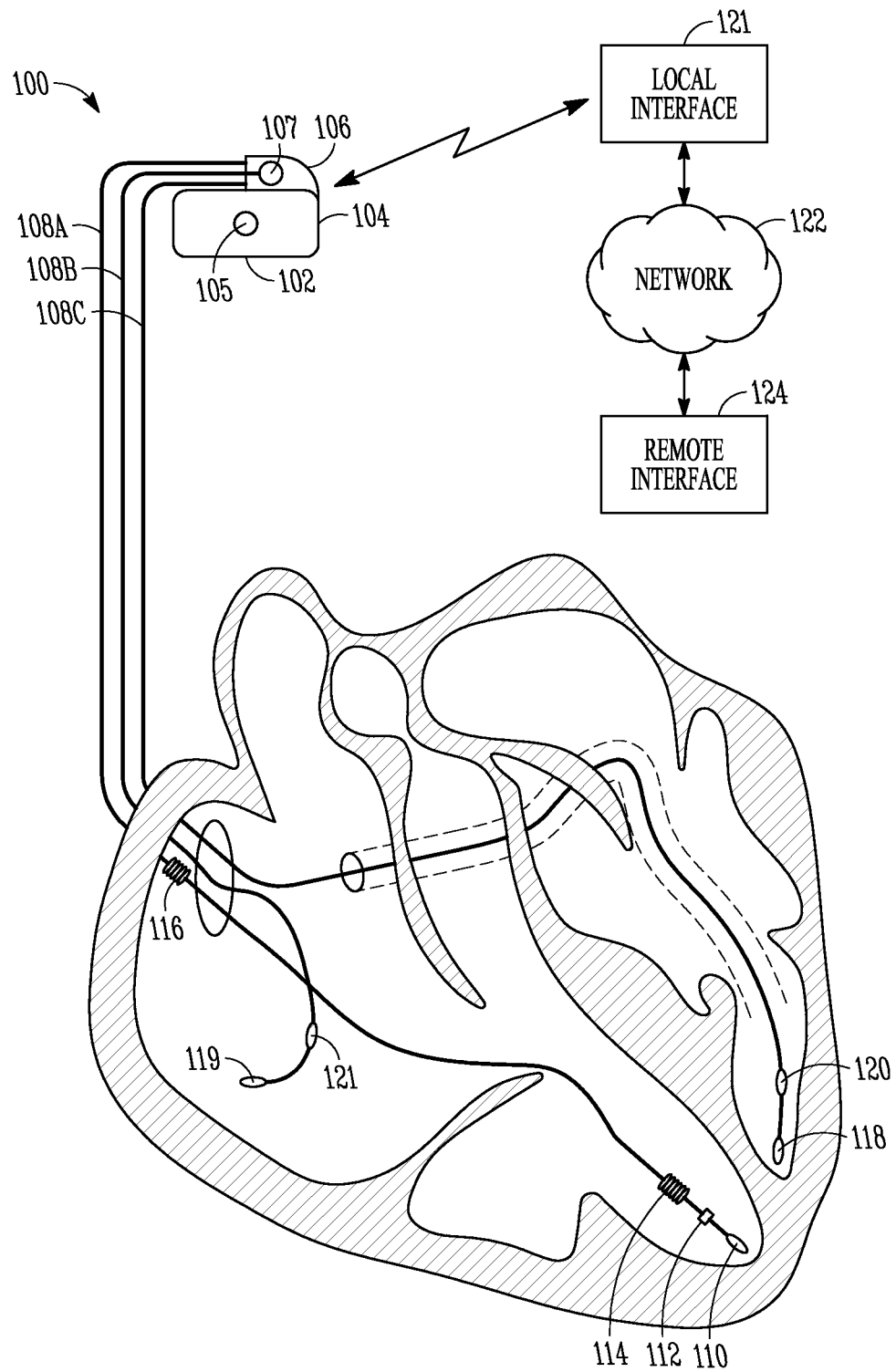
FIG. 1 shows an example of an implantable or other ambulatory cardiac rhythm management (CRM) device.

FIG. 1 shows an example of an implantable or other ambulatory cardiac rhythm management (CRM) device 100, such as for monitoring cardiovascular function, providing cardiovascular therapy, or both. In an example, the CRM device 100 can include an electronics unit 102 that can include a hermetically-sealed biocompatible housing 104 and a header 106 extending therefrom. The housing 104 can carry a power source and electronics. The header 106 can include one or more receptacles, such as for receiving the proximal ends of intravascular leads 108A-C. In an example, the lead 108A can be an intravascular RV lead that can extend from the superior vena cava (SVC) into the right atrium (RA), and then into the right ventricle (RV). The lead 108A can include an RV apical tip electrode 110, a slightly more proximal RV ring electrode 112, a still slightly more proximal RV shock coil electrode 114, and an even more proximal RA or SVC shock coil electrode 116. The various electrodes can be used for delivering electrical energy or sensing intrinsic electrical heart signals. An intravascular CS/LV lead 108C can extend from the SVC into the RA, through a coronary sinus (CS) into the coronary vasculature, such as near a portion of a left ventricle (LV). In an example, this second CS/LV lead 108B can include at least a distal electrode 118 and a proximal electrode 120, from which electrostimulation energies can be delivered or intrinsic electrical heart signals can be sensed. An intravascular right atrial (RA) lead 108B can extend from the SVC into the RA, and can include a distal electrode 119 and a proximal electrode 121. Other electrodes (e.g., a housing electrode 105 on the housing 104, a header electrode 107 on the header 106, an epicardial electrode, a subcutaneous electrode located away from the heart, or an electrode located elsewhere) or leads can be used.

In an example, an implantable CRM device 100 can include a communication circuit, such as to wireless communicate unidirectionally or bidirectionally with an external local interface 121, such as a CRM device programmer, repeater, handheld device, or the like. The local interface 121 can be configured to communicate via a wired or wireless computer or communication network 122 to a remote interface 124, such as a remote computer or server or the like.

Figure 2:
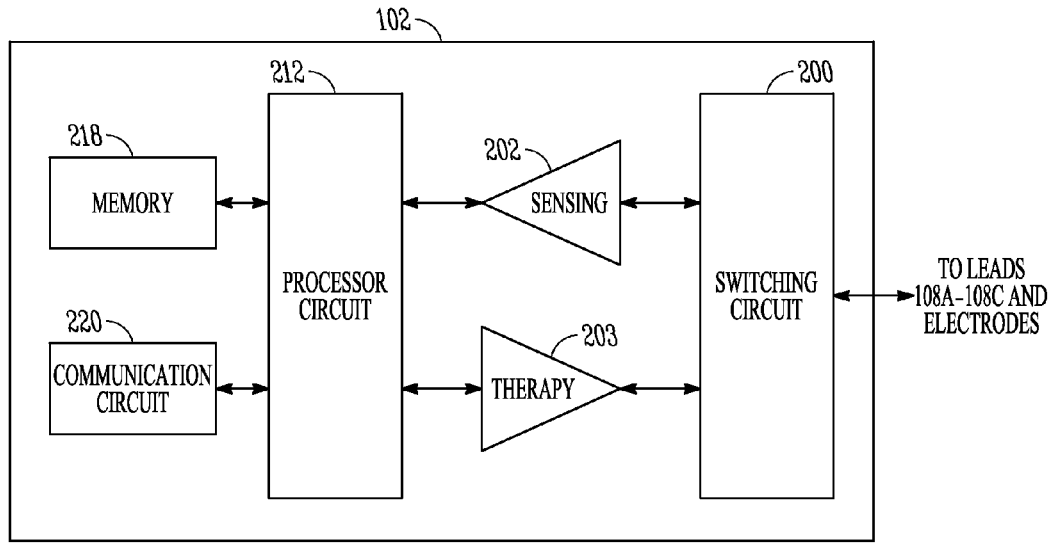
FIG. 2 shows an example of portions of the CRM device electronics unit.

FIG. 2 shows an example of portions of the CRM device electronics unit 102. In an example, this can include a switching circuit 200, such as for selectively connecting to the various electrodes such as on the leads 108A-C or elsewhere. A sensing circuit 202 can be selectively coupled to various electrodes by the switching circuit 200, and can include sense amplifiers, filter circuits, other circuits such as for sensing intrinsic electrical signals, such as intrinsic heart signals. A therapy circuit 203 can be selectively coupled to various electrodes by the switching circuit 200, and can include therapy energy generation circuitry (e.g., capacitive, inductive, or other) such as for generating, storing, or delivering an electrostimulation, cardioversion, defibrillation, or other energy. In an example, the sensing circuit 202 and the therapy circuit 203 can be coupled to a processor circuit 212. In an example, the processor 212 can perform instructions, such as for signal processing of signals derived by the sensing circuit 202 or the therapy circuit 203, or for controlling operation of other operations of the CRM device 100. The processor 212 can be coupled to or include a memory circuit 218, such as for storing or retrieving instructions or data, or a communication circuit 220, such as for communicating with the local interface 121.

Figure 3A:
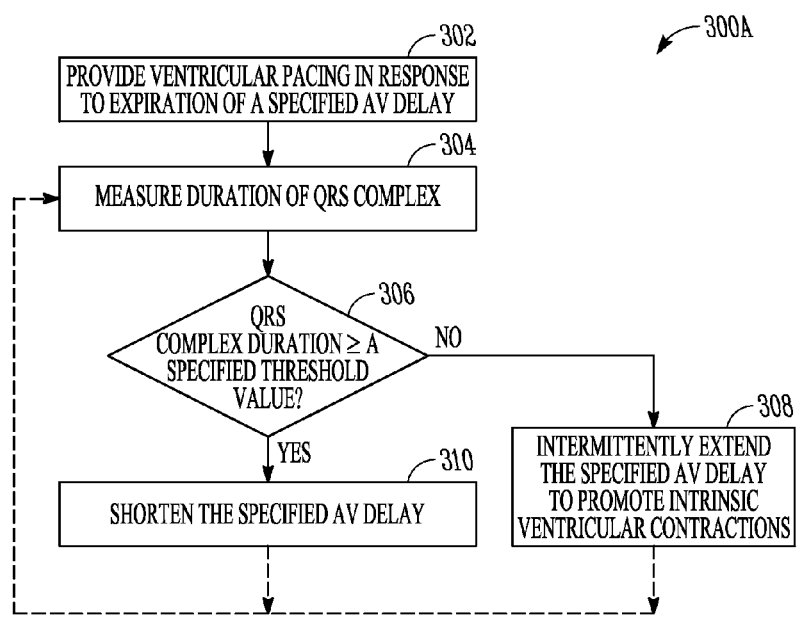
FIGS. 3A-C show examples of methods for providing physiologic demand driven pacing.

FIG. 3A shows an example of a method 300A for providing physiologic demand driven pacing. At 302, ventricular pacing can be provided in response to the expiration of a specified AV delay. In an example, the specified AV delay can be in the range of 40-400 milliseconds (ms). In an example, the specified AV delay can be set by the physician through an echocardiography-based optimization technique or through a system-based optimization algorithm, as described in Ding et al. U.S. Pat. No. 6,144,880 entitled "CARDIAC PACING USING ADJUSTABLE ATRIO-VENTRICULAR DELAYS," assigned to the assignee of the present application, the disclosure of which is incorporated herein by reference in its entirety. In an example, the ventricular pacing can be provided to a subject's right ventricle, left ventricle, or both ventricles (e.g., biventricular pacing). In an example, His-Purkinje Bundle pacing can be used instead of, or in addition to, biventricular pacing.

At 304, the duration of a QRS complex can be measured. The duration of the QRS complex can be measured using a shock channel or other wide vector channel, such as described in Kim et al. U.S. Pat. No. 6,708,058 entitled "NORMAL CARDIAC RHYTHM TEMPLATE GENERATION SYSTEM AND METHOD," assigned to the assignee of the present patent application, the disclosure of which is incorporated herein by reference in its entirety. In an example, the time difference between a sensed right ventricular contraction and a sensed left ventricular contraction within the same cardiac cycle can be measured instead of, or in addition to, the duration of the QRS complex. At 306, it can be determined whether the duration of the QRS complex is greater than or equal to a specified fixed or variable threshold value, or meets a similar detection criterion. In an example, the specified threshold value can be 120 ms. When the duration of the QRS complex is less than 120 ms, the QRS complex can be considered "narrow." When the duration of the QRS complex is greater than 120 ms, the QRS complex can be considered "wide." In an example, a narrow QRS complex can be considered physiologically normal, whereas a wide QRS complex can be indicative of abnormally slow ventricular activation due to either an arrhythmia originating outside the heart's normal conduction system (e.g., ventricular tachycardia) or abnormalities within the His-Purkinje system (e.g., supraventricular tachycardia). In addition, a wide QRS complex can be indicative of a bundle branch block or worsening heart failure status. In some patients, the duration of the QRS complex can change based on other factors, including changes in medication, diet, or activity, for example.

If, at 306, the duration of the QRS complex is less than the specified threshold value (e.g., narrow QRS), then, at 308, the specified AV delay can be intermittently extended in order to promote intrinsic ventricular contractions. In an example the specified AV delay can be extended by a specified percentage or by a set time period, such as 5-10 ms. In an example, intermittently extending the specified AV delay can include intermittently withholding the delivery of a ventricular pacing pulse. If intrinsic ventricular contractions occur in response to the extended AV delay, then ventricular pacing can be withheld until such intrinsic ventricular contractions cease to occur. However, if no intrinsic ventricular contractions occur in response to the extended AV delay, then ventricular pacing can resume using the specified AV delay.

If, at 306, the duration of the QRS complex is greater than or equal to the specified threshold value (e.g., wide QRS), then, at 310, the specified AV delay can be shortened. The specified AV delay can be shortened in order to prevent breakthrough intrinsic ventricular beats. It can be desirable to prevent breakthrough intrinsic ventricular beats when the QRS complex is wide because 100% biventricular pacing can be required in order to maintain ventricular synchrony and hemodynamic function of the heart. In an example the specified AV delay can be shortened by a specified percentage or by a set time period, such as 5-10 ms.

After the specified AV delay has been extended at 308 or shortened at 310, the process can optionally revert back to 304 (as indicated by the dotted lines), where monitoring of the QRS complex duration can continue on an ongoing basis, and adjustments to the AV delay can be made using information about the QRS complex duration, as described above. In an example, CRM device 100 can be configured to automatically adjust AV delay (e.g., by extending or shortening) based upon QRS complex duration, without the need for user input by a physician or other health care provider. In an example, CRM device 100 can be configured to provide information about at least one of the specified AV delay, the QRS complex, or ventricular pacing pulses to a user or automated process.

Figure 3B:
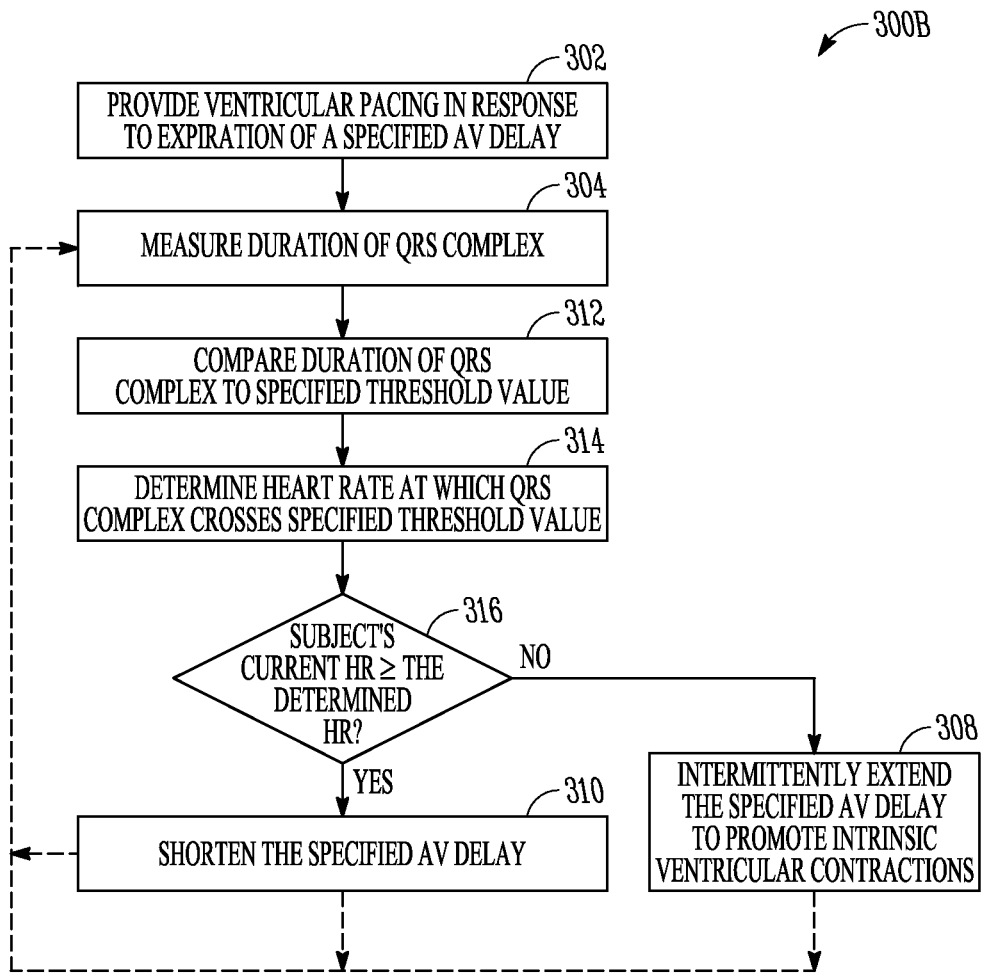

FIG. 3B shows an example of a method 300B for providing physiologic demand driven pacing. As described above with respect to FIG. 3A, at 302 ventricular pacing can be provided in response to the expiration of a specified AV delay, and at 304 the duration of the QRS complex can be measured. At 312, the duration of the QRS complex can be compared to a specified threshold value. In an example, the specified threshold value can be 120 ms. As described above with respect to FIG. 3A, when the duration of the QRS complex is less than the specified threshold value, the QRS complex can be considered "narrow," and when the duration of the QRS complex is greater than the specified threshold value, the QRS complex can be considered "wide."

At 314, the heart rate at which the QRS complex crosses the specified threshold value can be determined. In an example, the patient's heart rate can be measured concurrently with measurement of the QRS complex. At the time the QRS complex is equal to the specified threshold value, the patient's heart rate can be determined, recorded, and stored. This determined heart rate, corresponding to the QRS complex duration at the specified threshold value, can then be used as a comparison for subsequently measured heart rates. For example, at 316, the patient's current heart rate can be compared to the determined heart rate. If, at 316, the patient's current heart rate is less than the determined heart rate, then at 308, the specified AV delay can be intermittently extended in order to promote intrinsic ventricular contractions, as described above with respect to FIG. 3A. If, at 316, the patient's current heart rate is greater than or equal to the determined heart rate, then, then, at 310, the specified AV delay can be shortened, as described above with respect to FIG. 3A. After the specified AV delay has been extended at 308 or shortened at 310, the process can optionally revert back to 304 (as indicated by the dotted lines), where monitoring of the QRS complex duration can continue on an ongoing basis, as described above with respect to FIG. 3A.

Figure 3C:
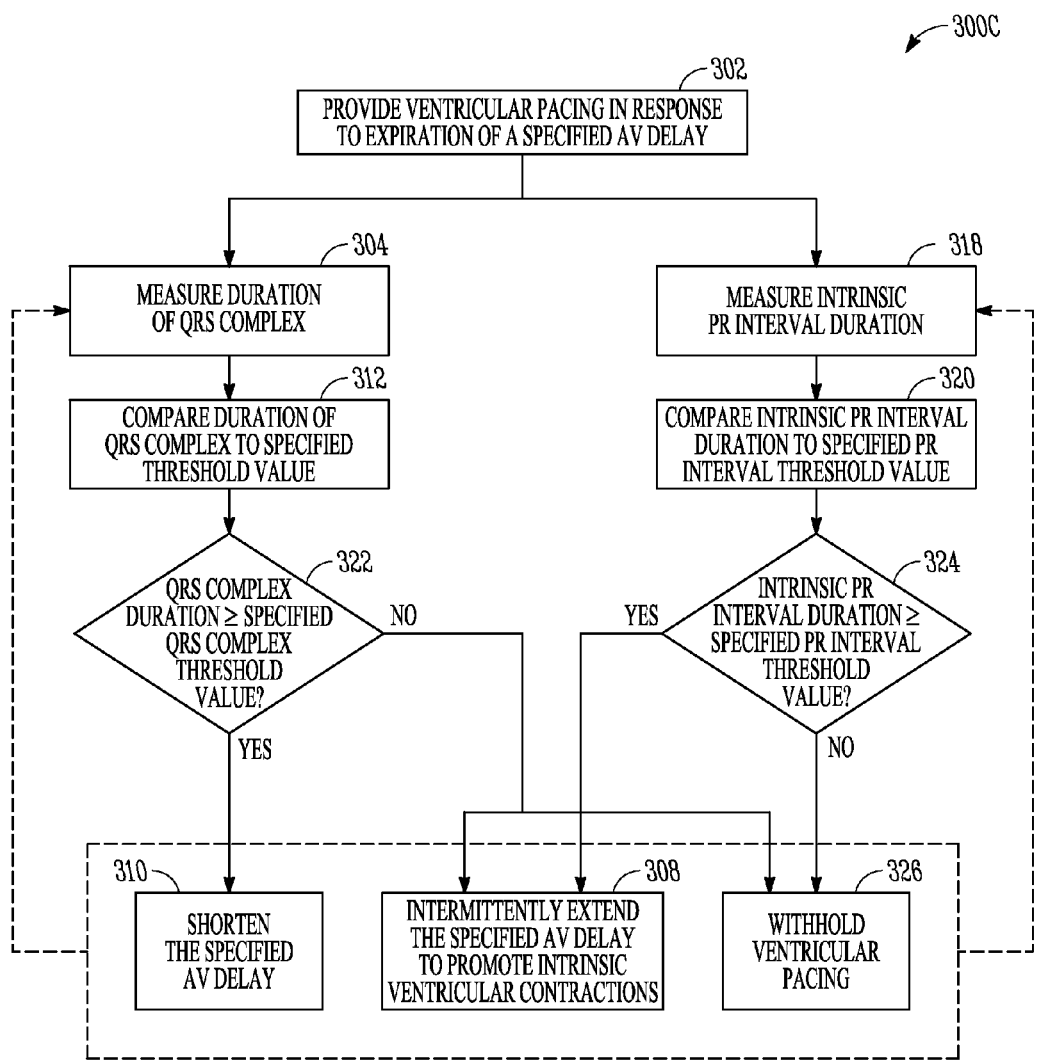

FIG. 3C shows an example of a method 300C for providing physiologic demand driven pacing. As described above with respect to FIG. 3A, at 302 ventricular pacing can be provided in response to the expiration of a specified AV delay, and at 304 the duration of the QRS complex can be measured. Concurrently with measurement of the duration of the QRS complex at 304, the duration of an intrinsic PR interval can be measured at 318. In an example, the intrinsic PR interval can represent the time it takes a cardiac electrical impulse to travel from the sinoatrial node, through the AV node, to the ventricles. Thus, the intrinsic PR interval can be a good estimate of AV node function. In an example, a prolonged PR interval can be indicative of an AV nodal block.

At 312, the duration of the QRS complex can be compared to a specified threshold value, as described above with respect to FIG. 3B. Similarly, at 320, the intrinsic PR interval duration can be compared to a specified PR interval threshold value. In an example, the specified PR interval threshold value can be 200 ms.

At 322, it can be determined whether the patient's QRS complex duration is greater than or equal to the specified QRS complex threshold value. Similarly, at 324, it can be determined whether the patient's intrinsic PR interval duration is greater than or equal to the specified PR interval threshold value. If, at 322, the patient's QRS complex duration is greater than or equal to the specified QRS complex threshold value, then at 310, the specified AV delay can be shortened, as described above with respect to FIG. 3A. If, at 322, the patient's QRS complex duration is less than the specified QRS complex threshold value, and, at 324, the patient's intrinsic PR interval duration is greater than or equal to the specified PR interval threshold value, then, at 308, the specified AV delay can be intermittently extended in order to promote intrinsic ventricular contractions, as described above with respect to FIG. 3A. If, at 322, the patient's QRS complex duration is less than the specified QRS complex threshold value, and, at 324, the patient's intrinsic PR interval duration is less than the specified PR interval threshold value, then, at 326, ventricular pacing can be withheld in order to allow intrinsic ventricular contractions to occur.

After the specified AV delay has been extended at 308 or shortened at 310, or ventricular pacing has been withheld at 326, the process can optionally revert back to 304 and 318 (as indicated by the dotted lines), where monitoring of the QRS complex duration and intrinsic PR interval duration can continue on an ongoing basis, and adjustments to the AV delay can be made using information about the QRS complex duration and intrinsic PR interval duration, as described above. In an example, CRM device 100 can be configured to automatically adjust AV delay (e.g., by extending or shortening) based upon QRS complex duration and intrinsic PR interval duration, without the need for user input by a physician or other health care provider.

Figure 4:
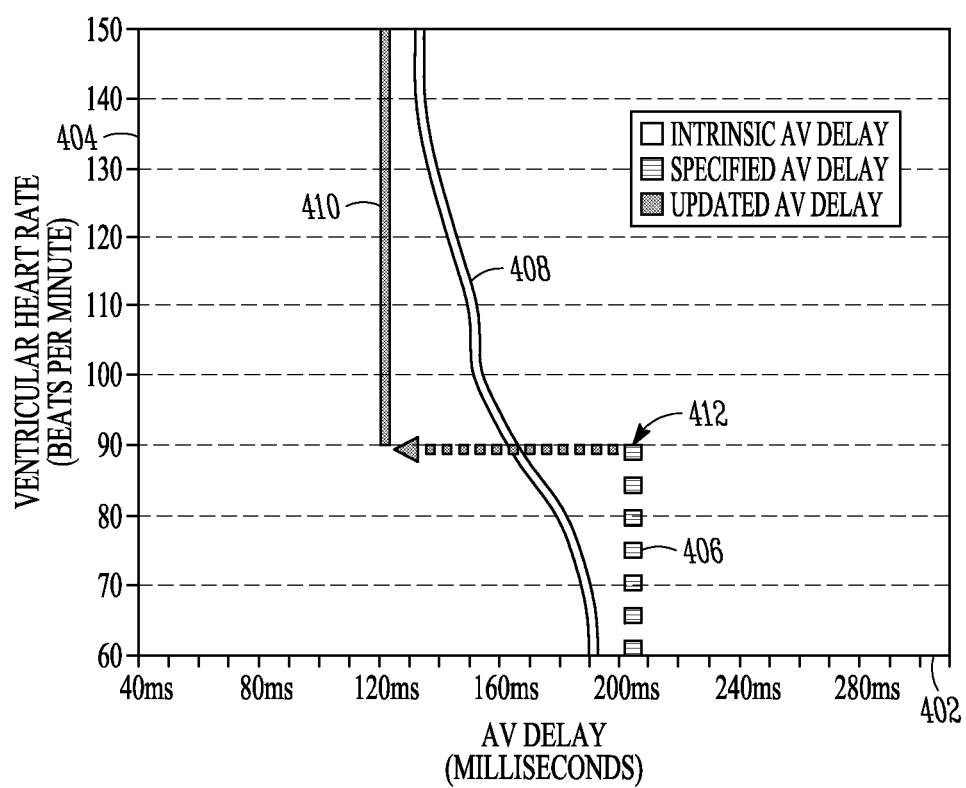
FIG. 4 shows an example of a plot of AV delay versus ventricular heart rate.

FIG. 4 shows an example of a plot of AV delay versus ventricular heart rate. The x-axis 402 represents AV delay measured in milliseconds (ms). The y-axis 404 represents ventricular heart rate measured in beats per minute (bpm). Line 406 represents the specified AV delay, which can be automatically or manually programmed into CRM device 100. In this example, the specified AV delay is about 205 ms. Line 408 represents the patient's intrinsic AV delay (or intrinsic PR interval) at various ventricular heart rates. Line 410 represents the updated, or shortened, AV delay at various ventricular heart rates.

Though not shown on this plot, at ventricular heart rates corresponding to line 406 (e.g., ventricular heart rates under 90 bpm), the duration of the patient's QRS complex can be classified as "narrow," as discussed above with respect to FIG. 3A. Additionally, at ventricular heart rates corresponding to line 410 (e.g., ventricular heart rates greater 90 bpm), the duration of the patient's QRS complex can be classified as "wide," as discussed above with respect to FIG. 3A. In this example, at line 406, when ventricular heart rates are under 90 bpm and the QRS complex duration is narrow, the specified AV delay can be intermittently extended to promote intrinsic ventricular contractions, as described above with respect to FIG. 3A. The arrow at 412 can be indicative of the ventricular heart rate (e.g., 90 bpm) at which the QRS complex duration switches from narrow to wide. At this point, the specified AV delay can be shortened, so as not to allow any intrinsic ventricular contractions to occur, as described above with respect to FIG. 3A. Thus, in this example, when the patient's ventricular heart rate is 90 bpm or above, then a shortened AV delay can be used, as shown at line 410. In an example, the QRS complex duration and the patient's corresponding heart rate can be monitored on an ongoing basis, and information about these parameters can be used to adjust (e.g., extend or shorten) the specified AV delay.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first,"

"second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The claimed invention is:

1. An apparatus comprising:
    a first data input configured to receive an intrinsic electric cardiac signal produced by the heart and to measure a duration of an intrinsic electrical QRS complex using the electric cardiac signal;
    a second data input configured to receive a subject heart rate;
    ventricular pacing circuitry configured to provide ventricular pacing pulses in response to expiration of a specified atrioventricular (AV) delay; and
    control circuitry configured to use information about the duration of the QRS complex to:
        determine a first specified threshold value using information about the intrinsic electrical QRS complex;
        compare a subject's heart rate to the first specified threshold value; and
        when the subject's heart rate is less than the first specified threshold value, intermittently extend the specified AV delay by an amount that obtains respective intrinsic ventricular contractions; and
        when the subject's heart rate is greater than or equal to the first specified threshold value, shorten the specified AV delay to provide a shortened AV delay, wherein the shortened AV delay is less than the specified AV delay.

2. The apparatus of claim 1, wherein the control circuitry is configured to intermittently extend the specified AV delay when the duration of the QRS complex is less than a second specified threshold value.

3. The apparatus of claim 1, wherein the control circuitry is configured to shorten the specified AV delay when the duration of the QRS complex is greater than a second specified threshold value.

4. The apparatus of claim 1, wherein the control circuitry is configured to use the duration of the QRS complex to automatically adjust at least one of extending or shortening the specified AV delay.

5. The apparatus of claim 1,
    wherein the control circuitry is configured to:
        compare the duration of the QRS complex to a second specified threshold value;
        determine a heart rate associated with the second specified threshold value; and
        use the heart rate associated with the second specified threshold value to determine the first specified threshold value; and
        when the subject's heart rate is greater than or equal to the second specified threshold value, provide ventricular pacing pulses in response to expiration of the shortened AV delay.

6. The apparatus of claim 5, wherein the control circuitry is configured to determine a heart rate associated with the second specified threshold value by determining a heart rate measured concurrently with the duration of the QRS complex when the duration of the QRS complex is equal to the second specified threshold value.

7. The apparatus of claim 1, comprising a third data input configured to receive an intrinsic PR interval duration; and
    wherein the control circuitry is configured to:
        compare the intrinsic PR interval duration to a third specified threshold;
        compare the duration of the QRS complex to a second specified threshold;
        when the PR interval duration is less than the third specified threshold and the duration of the QRS complex is less than the second specified threshold, withhold ventricular pacing pulses;
        when the PR interval duration is greater than the third specified threshold and the duration of the QRS complex is less than the second specified threshold, intermittently extend the specified AV delay by an amount that obtains respective intrinsic ventricular contractions; and
        when the duration of the QRS complex is greater than the second specified threshold, provide ventricular pacing pulses in response to expiration of the shortened AV delay, wherein the shortened AV delay is less than the specified AV delay.

8. The apparatus of claim 7, wherein the control circuitry is configured to use the PR interval duration and the duration of the QRS complex to automatically adjust at least one of extending or shortening the specified AV delay.

9. The apparatus of claim 1, wherein ventricular pacing pulses provided by the ventricular pacing circuitry include ventricular pacing pulses provided to at least one of a left ventricle or a right ventricle.

10. The apparatus of claim 1, comprising a user interface, coupled to the control circuitry to receive information about at least one of the QRS complex, the specified AV delay, or ventricular pacing pulses, and to provide the information to a user or automated process.

11. A non-transitory device-readable medium including instructions that, when performed by the device, comprise:
    receiving an intrinsic electric cardiac signal produced by the heart;
    measuring a duration of an intrinsic electrical QRS complex using the intrinsic electric cardiac signal produced by the heart;
    providing a first specified threshold value using information about the intrinsic electrical QRS complex;
    receiving a subject heart rate;
    providing ventricular pacing pulses in response to expiration of a specified atrioventricular (AV) delay; and
    using information about the duration of the QRS complex and the subject heart rate to:
        intermittently extend the specified AV delay that obtains respective intrinsic ventricular contractions when the subject's heart rate is less than the first specified threshold; and shorten the specified AV delay to provide a shortened AV delay when the subject's heart rate is greater than or equal to the first specified threshold value, wherein the shortened AV delay is less than the specified AV delay.

12. The non-transitory device-readable medium of claim 11, comprising intermittently extending the specified AV delay when the duration of the QRS complex is less than a second specified threshold value.

13. The non-transitory device-readable medium of claim 11, comprising shortening the specified AV delay when the duration of the QRS complex is greater than a second specified threshold value.

14. The non-transitory device-readable medium of claim 11, comprising using the duration of the QRS complex to automatically adjust at least one of extending or shortening the specified AV delay.

15. The non-transitory device-readable medium of claim 11, comprising:
   comparing the duration of the QRS complex to a second specified threshold value;
   determining a heart rate associated with the second specified threshold value;
   using the heart rate associated with the second specified threshold value to determine the first specified threshold value; and
   when the subject's heart rate is greater than or equal to the second specified threshold value, providing ventricular pacing pulses in response to expiration of the shortened AV delay.

16. The non-transitory device-readable medium of claim 15, comprising determining a heart rate associated with the second specified threshold value by determining a heart rate measured concurrently with the duration of the QRS complex when the duration of the QRS complex is equal to the second specified threshold value.

17. The non-transitory device-readable medium of claim 11, comprising:
   measuring an intrinsic PR interval duration;
   comparing the intrinsic PR interval duration to a third specified threshold;
   comparing the duration of the QRS complex to a second specified threshold;
   when the PR interval duration is less than the third specified threshold and the duration of the QRS complex is less than the second specified threshold, withholding ventricular pacing pulses;
   when the PR interval duration is greater than the third specified threshold and the duration of the QRS complex is less than the second specified threshold, intermittently extending the specified AV delay by an amount that obtains respective intrinsic ventricular contractions; and
   when the duration of the QRS complex is greater than the second specified threshold, providing ventricular pacing pulses in response to expiration of the shortened AV delay, wherein the shortened AV delay is less than the specified AV delay.

18. The non-transitory device-readable medium of claim 17, comprising using the PR interval duration and the duration of the QRS complex to automatically adjust at least one of extending or shortening the specified AV delay.

19. The non-transitory device-readable medium of claim 11, wherein providing ventricular pacing pulses includes providing ventricular pacing pulses to at least one of a left ventricle or a right ventricle.

20. The non-transitory device-readable medium of claim 11, comprising providing information about at least one of the QRS complex, the specified AV delay, or ventricular pacing pulses to a user or automated process.

* * * * *